United States Patent [19]

Steiner et al.

[11] Patent Number: 5,521,209

[45] Date of Patent: May 28, 1996

[54] N-SUBSTITUTED AZABICYCLO[3.2.0]HEPTANE DERIVATIVES AS NEUROLEPTICS, THE PREPARATION AND USE THEREOF

[75] Inventors: Gerd Steiner, Kirchheim; Liliane Unger; Berthold Behl, both of Ludwigshafen; Hans-Juergen Teschendorf, Dudenhofen, all of Germany

[73] Assignee: BASF Aktiengesellschaft, Ludwigshafen, Germany

[21] Appl. No.: 356,181

[22] PCT Filed: Jun. 8, 1993

[86] PCT No.: PCT/EP93/01440

§ 371 Date: Dec. 16, 1994

§ 102(e) Date: Dec. 16, 1994

[87] PCT Pub. No.: WO94/00431

PCT Pub. Date: Jan. 6, 1994

[30] Foreign Application Priority Data

Jun. 19, 1992 [DE] Germany .................... 42 19 973.5

[51] Int. Cl.⁶ .................... A61K 31/40; C07D 209/52
[52] U.S. Cl. .................... 514/112; 514/408; 514/414; 546/276.7; 548/452; 548/466
[58] Field of Search .................... 514/408, 412, 514/414; 546/272; 548/452, 466

[56] References Cited

U.S. PATENT DOCUMENTS 3,328,390  6/1967  Grogan .................... 260/239
4,605,655  8/1986  Yevich et al. .................... 514/252

FOREIGN PATENT DOCUMENTS

| 190472 | 8/1986 | European Pat. Off. . |
| 400661 | 12/1990 | European Pat. Off. . |
| 410114 | 1/1991 | European Pat. Off. . |
| 1289845 | 4/1959 | Germany . |
| 2941880 | 4/1980 | Germany . |
| 881893 | 11/1958 | United Kingdom . |
| 2037745 | 7/1980 | United Kingdom . |
| 92/18480 | 4/1992 | WIPO . |

OTHER PUBLICATIONS

Oppolzer W., Achini R., Pfenninger E., Weber H. P. (1976). Helv. Chim. Acta 58(4) 1186–1202.

107–Azabicyclic Butyrophenones, Grogan et al., Jul. (1967) J. Med. Chem. pp. 621–623.

*Primary Examiner*—C. Warren Ivy
*Assistant Examiner*—Evelyn Huang
*Attorney, Agent, or Firm*—Keil & Weinkauf

[57] ABSTRACT

Compounds of the formula I

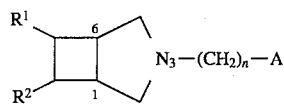

in which the substituents have the meanings stated in the description, and their preparation are described. The novel compounds are suitable for controlling diseases.

4 Claims, No Drawings

N-SUBSTITUTED AZABICYCLO[3.2.0]HEPTANE DERIVATIVES AS NEUROLEPTICS, THE PREPARATION AND USE THEREOF

This application is the national phase of PCT/EP93/01440 filed on Jun. 8, 1993.

The present invention relates to novel N-substituted azabicycloheptane derivatives, the preparation and use thereof for the preparation of drugs.

It is known that benzamide and butyrophenone derivatives with basic substituents have cerebroprotective and neuroleptic effects respectively (U.S. Pat. No. 4,605,655, EP 410 114, DE 1 289 845, EP 400 661, DE 2 941 880, EP 190 472).

In these cases it appears that the observed affinities for σ receptors are, besides the dopamine and serotonin affinities, particularly important.

We have now found that N-substituted 3-aza-bicyclo [3.2.0]heptane derivatives of the formula I

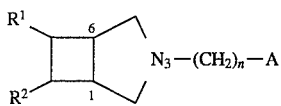

where

R$^1$ is a phenyl, pyridyl, thienyl or pyrrolyl group which is unsubstituted or mono- or disubstituted by halogen atoms, $C_1$–$C_4$-alkyl, trifluoromethyl, hydroxyl, $C_1$–$C_4$-alkoxy, amino, monomethylamino, dimethylamino, cyano or nitro groups, R$^2$ is a hydrogen atom or a phenyl group which is unsubstituted or substituted by halogen, methoxy, hydroxyl or amino, n is the number 1, 2, 3 or 4, A is a hydrogen atom or one of the radicals

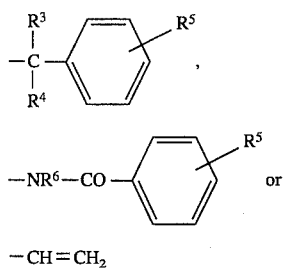

R$^3$ is a hydrogen atom, a hydroxyl radical or a phenyl radical which is unsubstituted or substituted by a fluorine, chlorine or bromine atom, R$^4$ is a hydrogen atom, or R$^3$ and R$^4$ together represent an oxygen atom, R$^5$ is a hydrogen, fluorine, chlorine or bromine atom or a hydroxyl, nitro, $C_1$–$C_4$-alkyl or methoxy group, and R$^6$ is a hydrogen atom or a methyl group, and salts thereof with physiologically tolerated acids have valuable pharmacological properties.

The substituents R$^1$ to R$^7$, and n, in the formula I preferably have the following meanings:

R$^1$: phenyl, unsubstituted or substituted by fluorine, chlorine, methoxy, trifluoromethyl, nitro, hydroxyl or amino R$^2$: hydrogen n: 2 and 3

R$^3$: hydroxyl, p-fluorophenyl

R$^4$: hydrogen or, together with R$^3$, oxygen

R$^5$: hydrogen, fluorine, chlorine

R$^6$: hydrogen, methyl.

The following compounds are particularly preferred:
1-(4-fluorophenyl)-4-[exo-6-phenyl-3-azabicyclo-[3.2.0] heptan-3-yl]butane-1-one,
1-(4-fluorophenyl)-4-[exo-6-p-fluorophenyl-3-aza-bicyclo[3.2.0]heptan-3-yl]butan-1-ol,
1-phenyl-4-[exo-6-phenyl-3-azabicyclo[3.2.0]- heptan-3-yl]-butan-1-one,
1-phenyl-4-[exo-6-p-fluorophenyl-3-azabicyclo-[3.2.0] heptan-3-yl]-butan-1-one,
1-(4-fluorophenyl)-4-[exo-6-phenyl-3-azabicyclo-[3.2.0] heptan-3-yl]butan-1-ol,
1-(4-fluorophenyl)-4-[exo-6-p-fluorophenyl-3-aza-bicyclo[3.2.0]heptan-3-yl]butan-1-ol,
1-phenyl-4-[exo-6-phenyl-3-azabicyclo[3.2.0]-heptan-3-yl]-butan-1-ol,
1-phenyl-4-[exo-6-p-fluorophenyl-3-azabicyclo[3.2.0] heptan-3-yl]-butan-1-ol,
1,1-bis(4-fluorophenyl)-4-[exo-6-phenyl-3azabicyclo
N-(3-[exo-6-phenyl-3-azabicyclo[3.2.0]heptan-3-yl]propyl)-4-fluorobenzamide,
N-(2-[exo-6-phenyl-3-azabicyclo[3.2.0]heptan-3-yl] ethyl)-4-fluorobenzamide,
N-(2-[exo-6-phenyl-3-azabicyclo[3.2.0]heptan-3-yl] ethyl)-N-methyl-4-fluorobenzamide,
N-(2-[exo-6-phenyl-3-azabicyclo[3.2.0]hetan-3-yl] ethyl)-N-methylbenzamide,
N-(3-[exo-6-p-fluorophenyl-3-azabicyclo[3.2.0]-heptan-3-yl]propyl)-4-fluorobenzamide,
N-(2-[exo-6-p-fluorophenyl-3-azabicyclo[3.2.0]-heptan-3-yl]ethyl)-benzamide and
N-(2-[exo-6-p-fluorophenyl-3-azabicyclo[3.2.0]-heptan-3-yl]ethyl)-N-methylbenzamide.

The compounds of the formula I according to the invention can be prepared by reacting a compound of the formula II

Nu-(CH$_2$)$_n$-A    (II), where A and n have the stated meanings, and Nu is a nucleofugic leaving group, with a 3-azabicyclo[3.2.0]heptane derivative of the formula III

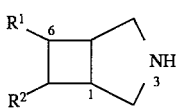

where

R$^1$ is a phenyl, pyridyl, thienyl or pyrrolyl group which is unsubstituted or mono- or disubstituted by halogen atoms, $C_1$–$C_4$-alkyl, trifluoromethyl, hydroxyl, $C_1$–$C_4$-alkoxy, amino, monomethylamino, dimethylamino, cyano or nitro groups, R$^2$ is a hydrogen atom or a phenyl group which is unsubstituted or substituted by halogen, methoxy, hydroxyl or amino, and converting the resulting compounds where appropriate into their addition salts with physiologically tolerated acids.

Suitable and preferred nucleofugic leaving groups for Nu are halogen atoms, in particular bromine or chlorine.

The reaction is expediently carried out in the presence of an inert base such as triethylamine or potassium carbonate to trap the acid and in an inert solvent such as a cyclic saturated ether, especially tetrahydrofuran or dioxane, or in an aromatic hydrocarbon such as toluene or xylene.

The reaction is, as a rule, carried out at from 20° to 150° C. and is generally complete within 1 to 10 hours.

The compounds of the formula I according to the invention can be purified either by recrystallization from conventional organic solvents, preferably from a lower alcohol such as ethanol, or by column chromatography.

Racemates can be fractionated into the enantiomers in a simple way by classical resolution using optically active carboxylic acids, e.g. tartaric acid derivatives, in an inert solvent, e.g. lower alcohols.

The free 3-azabicyclo[3.2.0]heptane derivatives of the formula I can be converted in the conventional way into the addition salt of a pharmacologically tolerated acid, preferably by mixing a solution with one equivalent of the appropriate acid. Examples of pharmaceutically acceptable acids are hydrochloric acid, phosphoric acid, sulfuric acid, methanesulfonic acid, sulfamic acid, maleic acid, fumaric acid, oxalic acid, tartaric acid and citric acid.

The compounds according to the invention have valuable pharmacological properties. They can be used as neuroleptics (especially atypical), antidepressants, sedatives, hypnotics, CNS protectives or muscle relaxants. It is possible for several of the said types of effect to occur in combination in a compound according to the invention. The pharmacological effect is detected both in vivo and in vitro and the substances can be characterized in particular by the affinity, which is in some cases very high and selective, for receptor subtypes, e.g. dopamine $D_1$, $D_2$, $D_3$ and $D_4$ receptors, serotonin 1A, 1D and 2 receptors, alpha 1 and 2 receptors, histamine 1 and muscarine receptors.

The following methods were used for the in vivo characterization of the novel substances:

a) Effect on orientation motility

Mice placed in a new environment show an exploratory behavior which is expressed by increased motor activity. This motor activity is measured in light-barrier cages for 0–30 min after the animals (female NMRI mice) have been placed in the cages. ED50: Dose which reduces the motor activity by 50% compared with placebo-treated controls.

b) Apomorphine antagonism

Female NMRI mice receive 1.21 mg/kg apomorphine s.c. At this dose, apomorphine causes motor activation which, when the animals are kept in wire mesh cages, is expressed by continuous climbing. The climbing is evaluated by the following scoring scheme (every 2 min for 30 min):

0: animal has four paws on the floor

1: animal has two paws on the wire

2: animal has four paws on the wire (is climbing).

The climbing behavior can be inhibited by pretreatment with antipsychotics. ED50: Dose which inhibits the climbing activity of the animals by 50% compared with placebo-treated controls.

c) L-5-HTP antagonism

Female Sprague-Dawley rats receive L-5-HTP in a dose of 316 mg/kg i.p. The animals then develop a state of agitation, and the signs of this forepawtreading and tremor are evaluated by a score (0 absent, 1 moderate, 2 pronounced) every 10 min in the period from 20 to 60 min after the L-5-HTP administration. The average score after L-5-HTP administration is 17. The test substances are administered orally 60 min before L-5-HTP. The ED50 is calculated as the dose which reduces the control score by 50% on average.

The stated methods are suitable for characterizing substances as antipsychotics. The inhibition of the L-5-HTP agitation reveals a serotonin-antagonistic effect, which is a type of effect characteristic of atypical neuroleptics.

The substances according to the invention show a good effect in these tests.

The invention accordingly also relates to a therapeutic composition which contains a compound of the formula I or its pharmacologically acceptable acid addition salt as active ingredient in addition to conventional excipients and diluents, and to the use of the novel compounds for controlling diseases.

The compounds according to the invention can be administered orally or parenterally, intravenously or intramuscularly, in a conventional way.

The dosage depends on the age, condition and weight of the patient and on the mode of administration. As a rule, the daily dose of active ingredient is from about 1 to 100 mg/kg of body weight on oral administration and from 0.1 to 10 mg/kg of body weight on parenteral administration.

The novel compounds can be administered in conventional solid or liquid pharmaceutical forms, e.g. as uncoated or (film-)coated tablets, capsules, powders, granules, suppositories, solutions, ointments, creams or sprays. These are produced in a conventional manner. The active ingredients can for this purpose be processed with conventional pharmaceutical aids such as tablet binders, fillers, preservatives, tablet disintegrants, flow regulators, plasticizers, wetting agents, dispersants, emulsifiers, solvents, release- slowing agents, antioxidants and/or propellent gases (cf. H. Sucker et al.: Pharmazeutische Technologie, Thieme Verlag, Stuttgart, 1978). The administration forms obtained in this way normally contain from 1 to 99 % by weight of active ingredient.

The substances of the formula II required as starting materials for synthesizing the novel compounds are known.

The substances of the formula III can be prepared by subjecting an amine of the formula IV

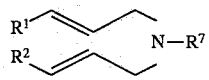

IV where $R^1$ and $R^2$ have the abovementioned meanings, and $R^7$ is hydrogen, acetyl, benzyl or trifluoroacetyl, to a photochemical 2+2 cycloaddition and subsequently eliminating an acyl or benzyl group where appropriate.

The photoreaction takes place well in an inert solvent, preferably acetone, at from 20° to 80° C. A particularly suitable light source is a high-pressure mercury lamp. It may be advantageous to carry out the photocycloaddition in a quartz apparatus under nitrogen atmosphere with the addition of about 1 mol of hydrochloric acid, per mol of amine.

The photocycloaddition is in most cases highly diastereoselective and gives the bicyclic compounds III with the exo configuration with respect to $R^1$ and R2:

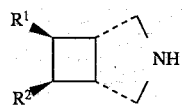

The two enantiomers can be isolated pure racemate resolution, e.g. using optically active tartaric acid derivatives.

The elimination of an acyl radical ($R^7$) is expediently effected by hydrolysis by conventional methods. A similar statement applies to the elimination of the benzyl radical.

The amines of the formula IV are disclosed in the literature or can be prepared either by reacting an aldehyde R1—CHO with vinylmagnesium chloride to give the allyl alcohol V

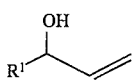

then carrying out a rearrangement with hydrogen chloride to give the allyl chloride VI

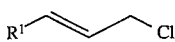

and finally reacting with the appropriate allylamine VII

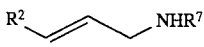

or by subjecting a cinnamaldehyde VIII

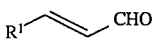

directly to reductive amination with the allylamine VII.

The following examples illustrate the invention:

A) PREPARATION OF THE STARTING MATERIALS 1. exo-6-(p-Fluorophenyl)-3-azabicyclo[3.2.0]heptane 19.4 g (102 mmol) of N-allyl-N-[3-(4-fluoro-phenyl)allyl]amine in 130 ml of acetone were mixed with 130 ml of 10% strength hydrochloric acid and with 600 mg of Michler's ketone and irradiated under nitrogen in a quartz apparatus with a 150 watt high-pressure mercury lamp for 55 h. The reaction mixture was then concentrated, and the residue was partitioned between methylene chloride and water. The aqueous phase was made alkaline with aqueous ammonia solution and then extracted twice more with methylene chloride. The combined organic phases were dried with sodium sulfate and concentrated. Yield 19.3 g (99%), melting point 165°–166° C. (maleate).

To separate the antipodes, 15.0 g (78.5 mmol) of the racemate were mixed with a solution of 31.7 g (78.5 mmol) of (−)-di-O-toluoyl-L-tartaric acid in 300 ml of boiling ethanol. The crystals (13.8 g) which separated out on cooling with stirring were filtered off with suction, washed with ethanol and recrystallized from 200 ml of ethanol with the addition of 200 ml of water. Liberation of the base provided the (+) antipode (5.5 g) with $[\alpha]_D=+97.0°$ (EtOH, c=0.969).

14.2 g of a salt crystallized out of the above mother liquor overnight and were recrystallized from 400 ml of ethanol (insolubles removed by filtration at the boiling points, and concentration to 300 ml). Liberation of the base yielded 4.0 g of the (−) antipode $[\alpha]_D=-96.0°$ (EtOH, c=0.940).

The exo-phenyl configurations were demonstrated by X-ray structural analysis.

2. exo-6-Phenyl-3-azabicyclo[3.2.0]heptane 50.0 g (28.9 mmol) of N-cinnamyl-N-allylamine in 1600 ml of acetone were mixed with 300 ml of 10% strength hydrochloric acid and irradiated under nitrogen in a quartz apparatus at room temperature with a 150 watt high-pressure mercury lamp for 48 h. The reaction mixture was then concentrated, and the residue was partitioned between methylene chloride and water. The aqueous phase was made alkaline with aqueous ammonia solution and then extracted twice more with methylene chloride. The combined organic phases were dried with sodium sulfate and concentrated. Yield 49.0 g (98%) of viscous oil, melting point 177°–178° C. (maleate).

3. exo-6,7-Diphenyl-3-benzyl-3-azabicyclo[3.2.0]heptane 70.0 g (206 mmol) of N,N-bis-cinnamylbenzylamine in 2500 ml of acetone were mixed with 0.8 g of Michler's ketone and irradiated under nitrogen in a borosilicate glass apparatus at room temperature with a 150 watt high-pressure mercury lamp for 25 h. The reaction mixture was then concentrated and the residue was partitioned between methylene chloride and water. The aqueous phase was made alkaline with aqueous ammonia solution and extracted twice more with methylene chloride. The combined organic phases were dried with sodium sulfate and concentrated. The crude product (65.0 g) was purified by column chromatography (silica gel, eluent toluene/ethanol 98/2) to yield 58.0 g (83%) of product, melting point 230°–232° C. (hydrochloride).

4. exo-6,7-Diphenyl-3-azabicyclo[3.2.0]heptane 16.0 g (254 mmol) of ammonium formate and 2.0 g of palladium (10%) on carbon were added to 12.0 g (35.4 mmol) of exo-6,7-diphenyl-3-benzyl-3-azabicyclo[3.2.0]heptane in a mixture of 300 ml of n-propanol and 16 ml of water, and the mixture was refluxed for 4 h (evolution of carbon dioxide). After cooling, the catalyst was filtered off with suction and washed with propanol and methylene chloride, and the filtrate was concentrated. The residue was partitioned between methylene chloride and water, and the aqueous phase was made alkaline with aqueous ammonia solution and extracted twice more with methylene chloride. The combined organic phases were dried with sodium sulfate and concentrated to give 8.1 g (92%) of product, melting point 140°–142° C. (maleate).

5. exo-6-Phenyl-3-benzyl-3-azabicyclo[3.2.0]heptane 9.2 g (35.0 mmol) of N-cinnamyl-N-allyl-benzylamine in 1100 ml of acetone were mixed with 100 mg of Michler's ketone and irradiated under nitrogen in a borosilicate glass apparatus at room temperature with a 150 watt high-pressure mercury lamp for 5 h. The reaction mixture was then concentrated. The crude product (9.4 g) was purified by column chromatography (silica gel, eluent methylene chloride/methanol 98/2) to yield 3.3 g (36%) of product, melting point 126°–128° C. (maleate).

6. 2,2,2-Trifluoro-1-[exo-6-(3-pyridyl)-3-azabicyclo[3.2.0]hept-3-yl]-ethanone 14.0 g (51.8 mmol) of N-allyl-N-[3-(3-pyridyl)[-allyl]-2,2,2-trifluoroacetamide were dissolved in 1.40 ml of acetone, and 30 ml of 10% strength aqueous hydrochloric acid were added and the mixture was irradiated under nitrogen in a boro-silicate glass apparatus at room temperature with a 150 watt high-pressure mercury lamp for 48 h. The reaction solution was then concentrated, taken up in 150 ml of water and adjusted to pH 8–9 with aqueous ammonia solution. The aqueous phase was extracted twice with tert-butyl methyl ether, and the combined organic phases were dried over sodium sulfate and concentrated. The residue was fractionated by column chromatography (silica gel, methylene chloride+2% methanol) to yield 6.2 g (42%) of unchanged N-allyl-N-[3- (3-pyridyl)allyl]-2,2,2-trifluoroacetamide and 3.7 g (26%) of 2,2,2-trifluoro-1-[exo-6-(3-pyridyl) -3-azabicyclo[3.2.0]hept-3-yl]ethanone as a dark oil.

7. exo-6-(3-Pyridyl)-3-azabicyclo[3.2.0]heptane 2.5 g of potassium hydroxide pellets were added to a solution of 3.7 g (13.7 mmol) of 2,2,2-trifluoro-1-[exo-6-(3-pyridyl)-3-azabicyclo -[3.2.0]hept-3-yl]ethanone in 50 ml of ethanol, and the solution was then stirred at room temperature for 2 h and subsequently poured into 100 ml of ice-water. The aqueous phase was extracted three times with tert-butyl methyl ether, and the combined organic phases were dried over sodium sulfate and concentrated. Yield 2.3 g (96%) of yellow oil, melting point 202°–205° C. (hydrochloride).

The following substances can be prepared in a similar way:

8. exo-6-(m-fluorophenyl)-3-azabicyclo[3.2.0]heptane
9. exo-6-(o-fluorophenyl)-3-azabicyclo[3.2.0]heptane, melting point 118°–120° C. (maleate)

10. exo-6-(p-chlorophenyl)-3-azabicyclo[3.2.0]heptane, melting point 152°–154° C. (maleate)
11. exo-6-(m-chlorophenyl)-3-azabicyclo[3.2.0] heptane, melting point 130°–132° C. (maleate)
12. exo-6-(p-methoxyphenyl)-3-azabicyclo[3.2.0]heptane
13. exo-6-(m-methoxyphenyl)-3-azabicyclo[3.2.0]heptane heptane
14. exo-6-(p-nitrophenyl)-3-azabicyclo[3.2.0]heptane, melting point 158°–160° C. (maleate)
15. exo-6-(m-nitrophenyl)-3-azabicyclo[3.2. 0]heptane
16. exo-6-(p-trifluoromethylphenyl)-3-azabicyclo[3.2.0] heptane, melting point 155°–156° C. (maleate)
17. exo-6-(m-trifluoromethylphenyl)-3-azabicyclo[3.2.0] heptane
18. exo-6-(3,4-dichlorophenyl)-3-azabicyclo[3.2.0]heptane
19. exo-6-(3,5-dichlorophenyl)-3-azabicyclo[3.2.0]heptane, melting point>250° C. (hydrochloride)
20. exo-6-(3,4-dimethoxyphenyl)-3-azabicyclo[3.2.0]heptane
21. exo-6-(m-hydroxyphenyl)-3-azabicyclo[3.2.0]heptane
22. exo-6-(p-hydroxyphenyl)-3-azabicyclo[3.2.0]heptane
23. exo-6-(3,4-dihydroxyphenyl)-3-azabicyclo[3.2.0 ]heptane
24. exo-6-(p-methylphenyl)-3-azabicyclo[3.2.0]heptane
25. exo-6-(m-methylphenyl)-3-azabicyclo[3.2.0]heptane
26. exo-6-(p-t-butylphenyl)-3-azabicyclo[3.2.0 ]heptane, melting point>255° C. (hydrochloride)
27. exo-6-(m-aminophenyl)-3-azabicyclo[3.2.0]heptane
28. exo-6-(p-aminophenyl)-3-azabicyclo[3.2.0]heptane
29. exo-6-(p-cyanophenyl)-3-azabicyclo[3.2.0]heptane, melting point 168°–170° C. (maleate)
30. exo-6-(2-thienyl)-3-azabicyclo[3.2.0]heptane, melting point 180°–182° C. (hydrochloride)
31. exo-6-(3-thienyl)-3-azabicyclo[3.2.0 ]heptane, melting point 143°–145° C. (hydrochloride)
32. exo-6-(5-chloro-2-thienyl)-3-azabicyclo[3.2.0]heptane, melting point 156°–157° C. (maleate)
33. exo-6-(2-pyrrolyl)-3-azabicyclo[3.2.0]heptane
34. exo-6-(4-pyridyl)-3-azabicyclo[3.2.0]heptane
35. exo-6-(2-pyridyl)-3-azabicyclo[3.2.0]heptane.

B) PREPARATION OF THE FINAL PRODUCTS

EXAMPLE 1

1-(4-Fluorophenyl)-4-[exo-6-phenyl-3-azabicyclo[3.2.0]heptan-3-yl]butan-1-one x HCl 8.65 g (50 mmol) of exo-6-phenyl-3-azabicyclo[3.2.0]heptane in 130 ml of xylene were mixed with 10.2 ml (60 mmol) of ω-chloro-4-fluorobutyrophenone and with 11.5 g (80 mmol) of finely powdered potassium carbonate in addition of 0.5 g of potassium iodide and refluxed with efficient stirring for 7 h. After cooling and concentration in a rotary evaporator the residue was partitioned between methylene chloride and water.

The aqueous phase was then extracted twice with methylene chloride and subsequently the organic phase was washed once with water, dried with sodium sulfate and concentrated. The crude product (21 g) was purified by column chromatography (silica gel, eluent methylene chloride/methanol 96/4). The free base was taken up in 200 ml of ether, the solution was filtered to remove insoluble material and then excess ethereal hydrochloric acid was added. The solid hydrochloride was then filtered off in the cold and washed copiously with ether to result in 8.3 g (45%) of product, melting point 169°–171° C.

The following can be prepared in a similar way:
2. 1-phenyl-4-[exo-6-phenyl-3-azabicyclo[3.2.0]-heptane-3-yl]butane-1-one, melting point 134°–136° C. (hydrochloride)
3. 1-(4-fluorophenyl)-4-[exo-6,7-diphenyl-3-azabicyclo[3.2.0]heptane-3-yl]butan-1-one, melting point 174°–176° C. (hydrochloride)
4. 1-(4-fluorophenyl) -4- [exo-6-phenyl-3-azabicyclo [3.2.0] heptan-3-yl]butane, melting point 131°–133° C. (hydrochloride)
5. 1-phenyl-2-[exo-6-phenyl-3-azabicyclo[3.2.0]heptan-3-yl]ethan-1-one, oil
6. 1-(4-fluorophenyl)-4-[exo-6-p-fluorophenyl-3-azabicyclo[3.2.0]heptan-3-yl]butane
7. 1-(4-fluorophenyl)-4-[exo-6-m-fluorophenyl-3-azabicyclo[3.2.0]heptan-3-yl]butan-1-one
8. 1-(4-fluorophenyl)-4-[exo-6-o-fluorophenyl-3-azabicyclo[3.2.0]heptan-3-yl]butan-1-one, melting point 180°–182° C. (hydrochloride)
9. 1- (4-fluorophenyl)-4-[exo-6-p-chlorophenyl-3-azabicyclo[3.2.0]heptan-3-yl]butane-1-one
10. 1-(4-fluorophenyl)-4-[exo-6-m-chlorophenyl-3-azabicyclo[3.2.0]heptan-3-yl]butan-1-one, melting point 137°–139° C. (hydrochloride)
11. 1-(4-fluorophenyl) -4-[exo-6-p-methoxyphenyl-3-azabicyclo[3.2.0 ]heptan-3-yl]butane-1-one
12. 1-(4-fluorophenyl)-4-[exo-6-m,p-dichlorophenyl-3-azabicyclo[3.2.0]heptan-3-yl]butan-1-one
13. 1-(4-fluorophenyl)-4-[exo-6-m,p-dimethoxyphenyl-3-azabicyclo[3.2.0]heptan-3-yl]butane-1-one.

EXAMPLE 14

1-(4-Fluorophenyl)-4-[exo-6-p-fluorophenyl-3-azabicyclo[3.2.0]heptane-3-yl]butan-1-one x HCl 4.5 g (23.5 mmol) of exo-6-p-fluorophenyl-3-azabicyclo[3.2.0]heptane in 50 ml of toluene were mixed with 6.0 g (30 mmol) of ω-chloro-4-fluorobutyrophenone and with 4.2 g (30 mmol) of finely powdered potassium carbonate plus 0.5 g of potassium iodide and refluxed with efficient stirring for 7 h. After cooling and concentration in a rotary evaporator the residue was partitioned between methylene chloride and water.

The aqueous phase was then extracted twice with methylene chloride and subsequently the organic phase was washed once with water, dried with sodium sulfate and concentrated. The crude product (9.4 g) was purified by column chromatography (silica gel, eluent methylene chloride/methanol 96/4). The free base was taken up in 150 ml of ether, the solution was filtered to remove insoluble material and then excess ethereal hydrochloric acid was added. After addition of 10 ml of acetone the solid hydrochloride was then filtered off in the cold and washed copiously with ether to result in 4.9 g (53%) of product, melting point 166°–168° C.

The following can be prepared in a similar way:
15. 1-phenyl-4-[exo-6-p-fluorophenyl-3-azabicyclo[3.2.0] heptan-3-yl]butane-1-one, melting point 141°–143° C. (maleate)
16. 1-(4-fluorophenyl)-4-[exo-6-p-fluorophenyl-3-azabicyclo[3.2.0]heptane-3-yl]butane
17. 1-(4-fluorophenyl)-4-[exo-6-p-nitrophenyl-3-azabicyclo[3.2.0]heptane-3-yl]butan-1-one, melting point 68°–70° C. (hydrochloride)
18. 1-(4-fluorophenyl)-4-[exo-6-m-nitrophenyl-3-azabicyclo[3.2.0]heptan-3-yl]butan-1-one
19. 1-(4-fluorophenyl)-4-[exo-6-p-trifluoromethylphenyl-3-azabicyclo[3.2.0 ]heptan-3-yl butan-1-one, melting point 158°–161° C. (hydrochloride)
20. 1-(4-fluorophenyl)-4-[exo-6-p-cyanophenyl-3-azabicyclo[3.2.0]heptane-3-yl]butan-1-one 21. 1-(4-fluorophenyl)-4-[exo-6-(3-thienyl)-3-azabicyclo[3.2.0]heptan-3-yl]butan-1-one
22. 1-(4-fluorophenyl)-4-[exo-6-(3-pyridyl)-3-azabicyclo[3.2.0]heptan-3-yl]butan-1-one
23. 1-(4-fluorophenyl)-3-[exo-6-p-fluorophenyl-3-azabicyclo[3.2.0]heptan-3-yl]propan-1-one, melting point 151°–154° C. (hydrochloride)

EXAMPLE 24

1,1-bis (4-Fluorophenyl)-4-[exo-6-p-fluorophenyl-3-azabicyclo[3.2.0]heptan-3-yl]butane x HCl 5.0 g (26.2 mmol) of exo-6-p-fluorophenyl-3-azabicyclo[3.2.0]heptane in 80 ml of xylene were mixed with 8.8 g (28.4 mmol) of 1,1-bis(4-fluorophenyl)-4-chlorobutane and with 7.0 g (50.6 mmol) of finely powdered potassium carbonate plus 0.3 g of potassium iodide and refluxed with efficient stirring for 15 h. After cooling and concentration in a rotary evaporator the residue was partitioned between methylene chloride and water. The aqueous phase was then extracted twice with methylene chloride and subsequently the organic phase was washed once with water, dried with sodium sulfate and concentrated. The crude product (110 g) was purified by column chromatography (silica gel, eluent methylene chloride/methanol 96/4). The free base was taken up in 350 ml of ether, the solution was filtered to remove insoluble material and then excess ethereal hydrochloric acid was added. Concentration provided 4.9 g (40%) of product, melting point 49°–50° C.

The following can be prepared in a similar way:
25. 1,1-bis (4-fluorophenyl)-4-[exo-6-phenyl-3-azabicyclo[3.2.0]heptane-3-yl]butane, melting point 54°–55° C. as hydrochloride

EXAMPLE 26

1-(4-Fluorophenyl)-4-[exo-6-phenyl-3-azabicyclo[3.2.0]heptan-3-yl]butan-1-one 0.6 g (16 mmol) of sodium boranate was added in portions to 4.6 g (13.6 mmol) of 1-(4-fluorophenyl)-4-[exo-6-phenyl-3-azabicyclo[3.2.0]heptan-3-yl]butan-1-one in 60 ml of methanol. The mixture was then stirred at room temperature for 2 h and concentrated in a rotary evaporator. The residue was partitioned between methylene chloride and water at pH 10, the aqueous phase was extracted twice more with methylene chloride, and the combined organic phases were washed with water, dried with sodium sulfate and concentrated. The crude product (4.6 g) was purified by column chromatography (silica gel, eluent methylene chloride/methanol 96/4). The free base was taken up in 150 ml of ether, the solution was filtered to remove insoluble material, and excess ethereal hydrochloric acid was added. The solid hydrochloride was then filtered off in the cold and washed copiously with ethyl to result in 3.1 g (61%) of product, melting point 147°–149° C.

The following can be prepared in a similar way:
27. 1-(4-fluorophenyl)-4-[exo-6-p-fluorophenyl-3-azabicyclo[3.2.0]heptan-3-yl]butan-1-ol, melting point 128°–129° C. (hydrochloride)
28. 1-(4-fluorophenyl)-4-[exo-6,7-diphenyl-3-azabicyclo[3.2.0]heptan-3-yl]butan-1-ol, melting point 228°–231° C. (hydrochloride)
29. 1-phenyl-4-[exo-6-phenyl-3-azabicyclo[3.2.0]-heptan-3-yl]butan-1-ol, melting point 128°–129° C. (hydrochloride)
30. 1-phenyl-4-[exo-6-p-fluorophenyl-3-azabicyclo[3.2.0]heptan-3-yl]butan-1-ol
31. 1-(4-fluorophenyl)-4-[exo-6-o-fluorophenyl-3-azabicyclo[3.2.0]heptan-3-yl]butan-1-ol, melting point 167°–168° C. (hydrochloride)
32. 1-(4-fluorophenyl)-4-[exo-6-m-chlorophenyl-3-azabicyclo[3.2.0]heptan-3-yl]butan-1-ol, melting point 143°–145° C. (hydrochloride)
33. 1-(4-fluorophenyl)-4-[exo-6-p-trifluoromethylphenyl-3-azabicyclo[3.2.0]heptane-3-yl]butan-1-ol, melting point 145°–148° C. (hydrochloride)

EXAMPLE 34

1-(4-Fluorophenyl)-4-[exo-6-p-aminophenyl-3-azabicyclo[3.2.0]heptan-3-yl]butan-1-one 6.6 g (17.2 mmol) of 1-(4-fluorophenyl)-3-[exo-6-p-nitrophenyl-3-azabicyclo[3.2.0]heptan-3-yl]butan-1-one were dissolved in 200 ml of glacial acetic acid, and 1.7 g of palladium on carbon (10%) were added and the mixture was hydrogenated at room temperature under atmospheric pressure for 4 h. The catalyst was filtered off with suction and the mother liquor was concentrated, the residue was partitioned between methylene chloride and water, and the aqueous phase was made alkaline by stirring with concentrated ammonia solution and extracted twice with methylene chloride. The organic phase was dried and concentrated to result in 5.0 g of crude product which was purified by column chromatography (silica gel, eluent methylene chloride/methanol 95/5) to result in 2.2 g (36%) of 1-(4-fluorophenyl-4-[exo-6-p-aminophenyl-3-azabicyclo[3.2.0]heptan-3-yl]butan-1-one (melting point of the hydrochloride 136°–139° C.) and 1.4 g (23%) of 1-(4-fluorophenyl) -4-[exo-6-p-aminophenyl-3-azabicyclo[3.2.0]-heptan-3-yl]butan-1-ol (melting point of the hydrochloride 122°–125° C.).

EXAMPLE 35

N-(3-[exo-6-Phenyl-3-azabicyclo[3.2.0]heptan-3-yl]propyl)-4-fluorobenzamide 3.5 g (20 mmol) of exo-6-phenyl-3-azabicyclo[3.2.0]heptane in 40 ml of toluene were mixed with N-(3-chloropropyl)-4-fluorobenzamide and with 4.8 g (35 mmol) of finely powdered potassium carbonate plus 0.5 g of potassium iodide and refluxed with efficient stirring for 9 h. After cooling, the mixture was concentrated in a rotary evaporator and the residue was partitioned between methylene chloride and water. The aqueous phase was then extracted twice with methylene chloride and subsequently the organic phase was dried with sodium sulfate and concentrated., The crude product (8.4 g) was purified by column chromatography (silica gel, eluent methylene chloride/methanol 96/4). The purified free base was dissolved in a mixture of 100 ml of ether and 10 ml of acetone and, while cooling in ice and stirring, a solution of 1.6 g of maleic acid in acetone was slowly added dropwise. The precipitated salt was filtered off under nitrogen, washed with ether and dried under nitrogen to result in 4.9 g (70%) of hygroscopic product as maleate, melting point 122°–124° C.

The following can be prepared in a similar way:
36. N-(3-[exo-6-phenyl-3-azabicyclo[3.2.0]heptan-3-yl]propyl)benzamide, melting point 70°–72° C. (hydrochloride)
37. N-(2-[exo-6-phenyl-3-azabicyclo[3.2.0]heptan-3-yl]ethyl)-4-fluorobenzamide
38. N-(2-[exo-6-phenyl-3-azabicyclo[3.2.0]heptan-3-yl]ethyl)benzamide, melting point 89°–90° C.
39. N-(2-[exo-6-phenyl-3-azabicyclo[3.2.0]heptan-3-yl]ethyl)-N-methyl-4-fluorobenzamide, melting point 126°–128° C. (hydrochloride)

40. N-(2-[exo-6-phenyl-3-azabicyclo[3.2.0]heptan-3-yl]ethyl)-N-methylbenzamide, melting point 121°–122° C. (hydrochloride)
41. N-(2-[exo-6-phenyl-3-azabicyclo[3.2.0]heptan-3-yl]ethyl)-N-methyl-4-isopropylbenzamide, melting point 184°–185° C. (hydrochloride)
42. N-(3-[exo-6-phenyl-3-azabicyclo[3.2.0]heptan-3-yl]propyl)-4-chlorobenzamide
43. N-(2-[exo-6-p-trifluoromethylphenyl-3-azabicyclo[3.2.0]heptan-3-yl]ethyl) -4-chlorobenzamide, melting point 112°–114° C.
44. N-(3-[exo-6-phenyl-3-azabicyclo[3.2.0]heptan-3-yl]propyl)-3-methoxybenzamide
45. N-(3-[exo-6-phenyl-3-azabicyclo[3.2.0]heptan-3-yl]propyl)-3-nitrobenzamide
46. N-(3-[exo-6-p-fluorophenyl-3-azabicyclo[3.2.0]heptane-3-yl]propyl) -4-fluorobenzamide, melting point 160°–162° C. (hydrochloride)
47. N-(3-[exo-6-p-fluorophenyl-3-azabicyclo[3.2.0]heptan-3-yl]propyl) benzamide, melting point 177°–178° C. (hydrochloride)
48. N-(2-[exo-6-p-fluorophenyl-3-azabicyclo[3.2.0]heptan-3-yl]ethyl)-4-fluorobenzamide, melting point 111°–113° C.
49. N-(2-[exo-6-p-fluorophenyl-3-azabicyclo[3.2.0]heptan-3-yl]ethyl) benzamide, melting point 94°–950° C.
50. N-(2-[exo-6-p-fluorophenyl-3-azabicyclo[3.2.0]heptan-3-yl]ethyl)-N-methyl-4-fluorobenzamide, melting point 170°–171° C. (hydrochloride)
51. N-(2-[exo-6-p-fluorophenyl-3-azabicyclo[3.2.0]heptan-3-yl]ethyl)-N-methylbenzamide
52. N-(2-[exo-6-p-fluorophenyl-3-azabicyclo[3.2.0]heptan-3-yl]ethyl)-N-methyl-4-isopropylbenzamide, melting point 189°–190° C. (hydrochloride)
53. N-(3-[exo-6-p-fluorophenyl-3-azabicyclo[3.2.0]heptan-3-yl]propyl)-4-chlorobenzamide
54. N-(3-[exo-6-p-fluorophenyl-3-azabicyclo[3.2.0]heptan-3-yl]propyl)-3-methoxybenzamide
55. N-(3-[exo-6-p-fluorophenyl-3-azabicyclo[3.2.0]heptan-3-yl]propyl)-3-nitrobenzamide
56. N-(2-[exo-6-m-chlorophenyl-3-azabicyclo[3.2.0]heptan-3-yl]ethyl)-4-chlorobenzamide, melting point 96°–98° C.
57. N-(2-[exo-6-o-fluorophenyl-3-azabicyclo[3.2.0] heptan-3-yl]ethyl)-4-chlorobenzamide, melting point 91°–93° C.
58. N-(2-[exo-6-p-fluorophenyl-3-azabicyclo[3.2.0 ]heptan-3-yl]ethyl)-2-hydroxybenzamide, melting point 93°–95° C. (see also Example 59)

EXAMPLE 59

N-(2-[exo-6-m-Hydroxyphenyl-3-azabicyclo[3.2.0]heptan-3-yl]ethyl)-4-chlorobenzamide 13 ml (13 mmol) of boron tribromide (1M solution in methylene chloride) were added dropwise at room temperature to 4.2 g (11 mmol) of N-(2-[exo-6-m-methoxyphenyl-3-azabicyclo[3.2.0]heptan-3-yl]ethyl)-4-chlorobenzamide in 70 ml of methylene chloride, and the mixture was stirred overnight. After cooling, 100 ml of 2N ammonium hydroxide solution were added, the organic phase was separated off and the aqueous phase was extracted with methylene chloride. Drying and concentrating resulted in 4.5 g of crude product which was purified by column chromatography (silica gel, eluent methylene chloride/methanol 95/5) to result in 2.8 g (69%) of product, melting point 65°–68° C.

EXAMPLE 60 exo-3-n-Butyl-6-phenyl-3-azabicyclo[3.2.0]heptane maleate 3.5 g (20 mmol) of exo-6-phenyl-3-azabicyclo [3.2.0] heptane in 50 ml of tetrahydrofuran were mixed with 4.2 ml (30 mmol) of triethylamine and with 5.4 g (40 mmol) of n-butyl bromide and refluxed with efficient stirring for 9 h.

After cooling, the mixture was concentrated in a rotary evaporator and the residue was partitioned between methylene chloride and water.

The aqueous phase was extracted twice with methylene chloride and then the organic phase was dried with sodium sulfate and concentrated. The crude product (4.2 g) was purified by column chromatography (silica gel, eluent methylene chloride/methanol 96/4). The purified free base (3.1 g) was dissolved in 200 ml of ether and, while cooling in ice and stirring, the stoichiometric amount of maleic acid in acetone was slowly added dropwise. The precipitated salt was filtered off with suction under nitrogen, washed with ether and dried under nitrogen to result in 4.4 g ( 64%) of maleate, melting point 125°–126° C.

The following can be prepared in a similar way:

61. exo-3-methyl-6-phenyl-3-azabicyclo 8 3.2.0]heptane, melting point 129°–131° C. (maleate)
62. exo-3-methyl-6-p-fluorophenyl-3-azabicyclo[3.2.0]heptane
63. exo-3-n-propyl-6-p-fluorophenyl-3-azabicyclo[3.2.0]heptane
64. exo-3-methyl-6,7-diphenyl-3-azabicyclo[3.2.0]heptane, melting point 197°–198° C. (hydrochloride)
65. exo-3-n-propyl-6-m-hydroxyphenyl-3-azabicyclo[3.2.0] heptane (see also Example 59), melting point 148°–150° C. (hydrochloride)
66. exo-3-allyl-6-m-methoxyphenyl-3-azabicyclo[3.2.0 heptane, melting point 118°–120° C. (hydrochloride)
67. exo-3-phenethyl-6-p-fluorophenyl-3-azabicyclo[3.2.0] heptane, melting point 128°–129° C. (maleate)

We claim:

1. An N-substituted 3-azabicyclo[3.2.0]heptane derivative of the formula I

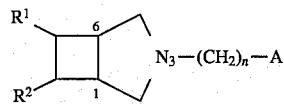

where $R^1$ is a phenyl, pyridyl, thienyl or pyrrolyl group which is unsubstituted or mono- or disubstituted by halogen atoms, $C_1$–$C_4$-alkyl, trifluoromethyl, hydroxyl, $C_1$–$C_4$-alkoxy, amino, monomethylamino, dimethylamino, cyano or nitro groups, $R^2$ is a hydrogen atom or a phenyl group which is unsubstituted or substituted by halogen, methoxy, hydroxyl or amino, n is the number 1, 2, 3 or 4, A is a hydrogen atom or one of the radicals

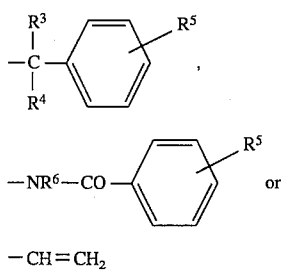

—NR⁶—CO—⟨phenyl⟩—R⁵    or

—CH=CH₂

R³ is a hydrogen atom, a hydroxyl radical or a phenyl radical which is unsubstituted or substituted by a fluorine, chlorine or bromine atom, R⁴ is a hydrogen atom, or R³ and R⁴ together represent an oxygen atom, R⁵ is a hydrogen, fluorine, chlorine or bromine atom or a hydroxyl, nitro, $C_1$–$C_4$-alkyl or methoxy group, and R⁶ is a hydrogen atom or a methyl group, and salts thereof with physiologically tolerated acids.

2. A method of treating a patient in need of an antipsychotic effect which comprises: administering to the patient an effective amount of a compound of the formula I as defined in claim 1.

3. The compound of the formula I as defined in claim 1 which is 1-(4-Fluorophenyl)-4-[exo-6-phenyl-3-azabicyclo [3.2.0]heptan-3-yl]butan-1-ol.

4. The compound of the formula I as defined in claim 1 which is N-(2-[exo-6-o-fluorophenyl-3-azabicyclo[3.2.0] heptane-3-yl]ethyl)-4-chlorobenzamide.

* * * * *